United States Patent

Zennaro et al.

[11] Patent Number: 6,096,790
[45] Date of Patent: Aug. 1, 2000

[54] PROCESS FOR THE PREPARATION OF A CATALYST BASED ON COBALT AND SCANDIUM

[75] Inventors: Roberto Zennaro; Andrea Gusso, both of Venice, Italy; Patrick Chaumette, Bougival, France

[73] Assignees: Agip Petroli S.p.A.; Eni S.p.A., both of Rome, Italy; Institut Francais du Petrole, Rueil-Malmaison, France

[21] Appl. No.: 09/147,737

[22] PCT Filed: Jun. 20, 1998

[86] PCT No.: PCT/EP98/03873

§ 371 Date: Mar. 18, 1999

§ 102(e) Date: Mar. 18, 1999

[87] PCT Pub. No.: WO99/00190

PCT Pub. Date: Jan. 7, 1999

[30] Foreign Application Priority Data

Jun. 26, 1997 [IT] Italy ................................. MI97A1510

[51] Int. Cl.[7] .......................... C07C 27/00; B01J 21/08; B01J 23/00; B01J 23/40
[52] U.S. Cl. .......................... 518/715; 518/700; 502/263; 502/314; 502/327
[58] Field of Search ...................................... 518/715, 700; 502/327, 263, 314

[56] References Cited

U.S. PATENT DOCUMENTS

| 4,585,798 | 4/1986 | Beuther et al. . |
| 5,856,365 | 1/1999 | Zennaro et al. ......................... 518/715 |

FOREIGN PATENT DOCUMENTS

| 0 756 895 | 2/1997 | European Pat. Off. . |
| WO 93/05000 | 3/1993 | WIPO . |
| WO 94/04476 | 3/1994 | WIPO . |

*Primary Examiner*—Johann Richter
*Assistant Examiner*—J. Parsa
*Attorney, Agent, or Firm*—Oblon, Spivak, McClelland, Maier & Neustadt, P.C.

[57] ABSTRACT

A process for the preparation of a catalyst comprising sequential deposition of cobalt or a cobalt compound, and scandium or a scandium compound, on an inert carrier oxide, which catalyst can be used in the conversion of synthesis gas according to the Fischer-Tropsch process.

16 Claims, No Drawings

PROCESS FOR THE PREPARATION OF A CATALYST BASED ON COBALT AND SCANDIUM

This application is a 371 of PCT/EP98103873 filed on Jun. 20, 1998.

The present invention relates to a process for the preparation of a catalyst and its use in the conversion of synthesis gas according to the Fischer-Tropsch process.

More specifically, the present invention relates to a process for the preparation of a catalyst comprising Co and Sc supported on an inert carrier.

The selection of cobalt is due to the fact that this favours the formation of paraffins with a high molecular weight preventing the formation of branched products, olefins and compounds containing oxygen.

The use of catalysts based on cobalt goes back to the first works of Fischer in 1932 (H. H. Storch, N. Golumbic, R. B. Anderson, "The Fischer Tropsch and Related Synthesis", John Wiley & son, Inc., New York, 1951, pages 345–367) which developed the $Co/ThO_2/MgO/kieselguhr$ system.

The evolution of these systems subsequently led to the idenfitication of various promoters to be coupled with cobalt in order to increase the selectivity to hydrocarbons with a high moleuclar weight, this mainly in the last twenty years. In fact, the increase in price of crude oil in the 70s' provided the incentive for exploring other ways of producing liquid fuels and chemicals.

U.S. Pat. No. 4,088,671 describes a catalyst for Fischer-Tropsch having cobalt and ruthenium as active ingredients, the former being present in a larger quantity with respect to the latter.

WO93/05000 describes a catalyst essentially consisting of cobalt (1–50% by weight), scandium (0.01–25% by weight) and an appropriate carrier selected from alumina, silica, silica-alumina, kieselguhr, prepared according to the usual preparation techniques among which impregnation of the carrier with aqueous solutions of the corresponding salts. The above catalyst, particularly efficient in the conversion of synthesis gas to give a hydrocarbon product with a high content of paraffins, has the disadvantage however of requiring high reaction temperatures and producing large quantities of methane.

A process has been found for the preparation of a catalyst, supported on an inert material, essentially consisting of a larger quantity of cobalt and a smaller quantity of scandium, which overcomes the drawbacks mentioned above. With this process, in fact, it is possible to obtain a supported catalyst based on cobalt and scandium which allows high conversions of CO to paraffins with a high molecular weight with low selectivities to methane, operating at lower temperatures than those described in WO 93/05000.

In accordance with this, the present invention relates to a process for the preparation of a catalyst comprising an inert carrier selected from at least one oxide of at least one element selected from Si, Ti, Al, Zr, Zn, Mg, Sn, preferably silicon, in the form of elements or oxides, a larger quantity of cobalt and smaller quantities of scandium, characterized in that it comprises at least the following steps:

1) production of a first catalytic precursor (A) containing cobalt and at least part of the inert carrier, by the deposition of cobalt on the inert carrier; subsequent calcination, reduction and passivation of the inert carrier containing cobalt;
2) production of the final catalyst by the deposition of scandium on the catalytic precursor (A); subsequent calcination, reduction and passivation of the inert carrier containing cobalt and scandium.

A further object of the present invention relates to the catalyst which can be obtained with the above process.

In the process of the present invention, step (1) consists in an initial deposition of cobalt on the inert carrier. This deposition, like that of the second element in step (2), can be carried out according to various techniques known to experts in the field, for example exchange, impregnation, dry impregnation (also called of the incipient imbibition), precipitation, gelation and mechanical mixing.

In the preferred embodiment, the deposition of cobalt in step (1) is carried out by the dry impregnation technique. According to this method the material to be impregnated is put in contact with a volume of solution more or less equal to the pore volume.

In step (1) it is preferable to use aqueous solutions of cobalt salts. Any kind of cobalt salts can be used, for example halides, nitrate, acetate, oxalate, the complex formed with lactic acid and lactates, the complex formed with tartaric acid and tartrates, the complex formed with another polyacid or hydroxyacid and the relative salts, the complex formed with acetylacetonates.

After depositing the desired quantity of cobalt salt, preferably cobalt nitrate, onto the inert carrier, a calcination step is carried out, followed by a reduction and passivation step. Optionally, before the calcination, the impregnated carrier is subjected to drying to eliminate most of the water. This drying can be carried out first at temperatures of between 10 and 30° C. and subsequently at temperatures of between 100 and 120° C., preferably in a stream of gas.

In step (1) the calcination is carried out at a temperature of between 300° C. and 500° C., preferably between 350° C. and 450° C., in an environment of air to eliminate all the organic residues.

The product thus calcined is then subjected to a reduction step in an environment essentially consisting of hydrogen, at a temperature of between 300° C. and 500° C., more preferably from 350° C. to 450° C. It is preferable to gradually bring the substrate to be calcined to this temperature, for example with a heating rate of between 3 and 20° C./minute. The reduction step is usually completed at the above temperature in a time of from 10 to 20 hours and with a stream of $H_2$ of between 1 and 3 liters/hour per gram of catalyst.

At the end of the reduction step, a passivation step is carried out in the presence of oxygen diluted with an inert gas, usually nitrogen, preferably carried out at a temperature of between 10° C. and 80° C. Using, for example, nitrogen containing 1–2% of $O_2$ (stream of 2 liters/hour), the above step can have a duration of from 1 to 5 hours at 25° C.

It is evident that at the end of the reduction (and obviously before the passivation), the sample must be cooled.

The second and last step of the process of the present invention consists in depositing the desired quantity of scandium onto the precursor (A), obtained at the end of the first step.

In one embodiment, a scandium nitrate is used, dissolved in solvent selected from acetone, lower alcohols, water and the relative mixtures. In step (2), the preferred technique is the wet impregnation, which essentially consists in immerging the precursor (A) into the solution of Scandium and eliminating the solvent with a slow evaporation system under vacuum.

As for step 1, after depositing the scandium, there is a calcination step followed by a reduction and subsequently a passivation step. In this case however, it is preferable to carry out the calcination step at a slightly lower temperature with respect to the calcination temperature of step 1, i.e. from 200° C. to 400° C., preferably from 205° C. to 350° C. The reduction and passivation on the other hand are carried out under the same temperature conditions as step 1.

The catalytic composition which can be obtained with the process of the present invention contains a larger quantity of cobalt (in metal form or in the form of a derivative) and a smaller quantity of scandium, as a metal or in the form of a derivative. Both the cobalt and the scandium are dispersed on the carrier and, when present in the form of a derivative, the oxide form is preferred.

As already specified, the carrier consists of at least one oxide selected from at least one of the following elements: Si, Ti, Al, Zr, Zn, Mg, Sn. In the preferred embodiment the inert carrier is silica.

The content of the above elements in the final catalyst, expressed as metal content and defined as weight percentage with respect to the weight of the catalyst, is from 1 to 50%, preferably from 5 to 35% for the Cobalt, whereas it is from 0.05 to 5%, preferably from 0.1 to 3% for the Scandium.

As already mentioned, the present invention also relates to a process for the preparation of hydrocarbons from synthesis-gas (Fischer-Tropsch process) in the presence of the catalytic system described above.

The present invention relates to a catalytic composition which allows the mixture of CO and $H_2$, known as synthesis gas, to be converted into essentially saturated and linear hydrocarbons having a $C_{25}^+$ content of between 25 and 29% by weight for hourly volumetric flow-rate values (GHSV= Gas Hourly Space Velocity) of between 500 and 1500 $h^{-1}$.

The conditions for using these catalysts are, in turn, those already known in the art for the embodiment of the Fischer-Tropsch synthesis.

The conversion of the synthesis gas to hydrocarbons takes place at a pressure normally between 0.1 and 15 MPa, preferably from 1 to 10 MPa, at a temperature generally within the range of 150° C. to 350° C., preferably from 170° C. to 300° C. A lowering of the reaction temperature generally causes an increase in the selectivity to hydrocarbon products with a high molecular weight, but an inevitable decrease in the conversion of the syngas (CO conversion). There are therefore selectivity and conversion limits governed by economic considerations which impose definite fields of practice under the reactions conditions to be used. These limits can be overcome by the use of particularly selective catalytic systems with respect to the hydrocarbon fractions with a high molecular weight (for example $C_{25}^+$).

The hourly volumetric velocity of the reagent gas is generally from 100 to 20000, preferably from 400 to 5000, volumes of synthesis gas per volume of catalyst and per hour; The ratio $H_2/CO$ in the synthesis gas is generally from 1:2 to 5:1, preferably from 1.2:1 to 2.5:1.

The catalyst can be used in the form of fine powder (about 10–700 mm) or in the form of particles having an equivalent diameter of from 0.7 to 10 mm, respectively in the presence of a liquid phase (under the operating conditions) and a gaseous phase, or a gaseous phase. The liquid phase can consist of at least one hydrocarbon having at least 5, preferably at least 10, carbon atoms per molecule. In the preferred embodiment, the liquid phase consists essentially of the same reaction product.

Just to give an example, the catalysts of the present invention can be used in a fixed-bed reactor, fed in continuous with a mixture of Co and $H_2$ and operating under the following conditions:

| | |
|---|---|
| - reaction temperature | 200–220° C. |
| - reaction pressure | 20 bars |
| - space velocity | 500–1500 $h^{-1}$ |
| - $H_2$/CO mixture | 2/1 |

Following these conditions, the catalysts prepared in examples 1 to 5 were evaluated and their compositions are summarized in table 1. The results of the reactivity tests are indicated in table 2.

EXAMPLE 1

Catalyst A (Reference)

Silica is used, having a surface area of 300 $m^2/g$, a specific pore volume of 1.3 $cm^3/g$, a particle diameter of 20 mm, a specific weight of 0.388 g/cc.

The above silica is dry impregnated with a nitric solution of $Co(NO_3)_2.6H_2O$ in such quantities as to obtain a percentage of Co equal to 15% by weight referring to the total. The silica thus impregnated is dried at 120° C. for 16 hours and calcined at 400° C. in air for 4 hours, then treated in a stream of $H_2$ at a space velocity (GHSV) of 1000 $h^{-1}$, in a tubular reactor at 400° C. for 16 hours. The sample thus reduced is passivated in a mixture of (1%) $O_2$/(99%) $N_2$ with GHSV at 1000 $h^{-1}$ for 2 hours at room temperature. (Catalyst A: Co/$SiO_2$; 15% Co).

EXAMPLE 2

Catalyst B

For the preparation of catalyst B, a solution of $Sc(NO_3)_2$ $10^{-3}$ M in acetone is added to 50 g of catalyst A, in such a volume as to obtain a final weight percentage of Sc equal to 0.1%.

The suspension thus obtained is left under stirring for two hours and is then dried under vacuum at 40° C. The sample is calcined at 300° C. for 4 hours in air, reduced at 400° C. in $H_2$ for 16 hours with a GHSV of 1000 h–1 at room temperature and passivated in (1%)$O_2$/(99%)$N_2$ with a GHSV of 1000 $h^{-1}$ for 2 hours at room temperature. (Catalyst B: Co/Sc/$SiO_2$ 15% Co, 0.1% Sc).

EXAMPLE 3

Catalyst C

The preparation of catalyst C differs from that described in example 2 in the use of a solution of $Sc(NO_3)_2$ $10^{-3}$ M in acetone in such a volume as to obtain a final weight percentage of scandium equal to 0.4%. (Catalyst C: Co/Sc/$SiO_2$ 15% Co, 0.4% Sc).

EXAMPLE 4

Catalyst D

The preparation of catalyst D differs from that described in example 2 in the use of a solution of $Sc(NO_3)_2$ $10^{-3}$ M in acetone in such a volume as to obtain a final weight percentage of scandium equal to 0.2%. (Catalyst D: Co/Sc/$SiO_2$ 15% Co, 0.2% Sc).

COMPARATIVE EXAMPLE 5

Catalyst E

This catalyst is prepared according to what is described in example 18 of WO 93/05000.

42.4 g of silica (surface area=540 $m^2/g$; average pore volume=0.9 cc/g; specific weight =0.42 g/cc) are used as carrier for the catalyst.

An aqueous solution of cobalt nitrate and scandium nitrate is then prepared by dissolving 20.83 g of $Co(NO_3)_2.6H_2O$ and 2 g of $Sc(NO_3)_2.5H_2O$ in water.

Following the impregnation technique, the carrier is impregnated with this solution and the solvent is eliminated with an evaporation system under vacuum (rotating evaporator), dried and calcined at 500° C. for 4 hours in muffle.

A product is obtained having a content of Co of 7.5% w/w and Sc of 0.5% w/w.

The characteristics of the catalysts thus prepared are indicated in table 1.

TABLE 1

| Example | Catalyst | % Co | % Sc | Carrier |
|---------|----------|------|------|---------|
| Comp. 1 | A | 15 | — | $SiO_2$ |
| 2 | B | 15 | 0.1 | $SiO_2$ |
| 3 | C | 15 | 0.4 | $SiO_2$ |
| 4 | D | 15 | 0.2 | $SiO_2$ |
| Comp. 5 | E | 7.5 | 0.5 | $SiO_2$ |

The catalysts thus prepared were tested for the Fischer-Tropsch reaction under the conditions specified above.

The results are shown in table 2.

TABLE 2

| | A | B | C | D(1) | D(2) | E |
|---|---|---|---|---|---|---|
| T(° C.) | 210 | 205 | 210 | 208 | 210 | 218 |
| Conv. CO (%) | 55.12 | 82.86 | 78.95 | 57.61 | 77.64 | 32.5 |
| Prod. $C_2^+$ (g/Kg/h) | 87.41 | 122.41 | 161.21 | 272.61 | 351.74 | 187.24 |
| Co-T-Y | 3.51 | 4.02 | 6.38 | 9.31 | 12.74 | 9.81 |
| Sel. $C_1$–$C_4$ | 20.57 | 20.95 | 19.37 | 17.25 | 22.3 | 24.05 |
| Sel. $C_{10}$–$C_{24}$ | 43.58 | 41.61 | 44.17 | 66.28 | 54.74 | 49.05 |
| Sel. $C_{25}^+$ | 23.77 | 23.55 | 24.96 | 7.83 | 5.52 | 4.19 |
| Sel. $C_5^+$ | 81.17 | 80.36 | 81.94 | 82.75 | 77.7 | 75.95 |
| Sel. $CO_2$ | 0.8 | 2.99 | 1.49 | 0.04 | 0.14 | 0.42 |
| GHSV | 500 | 500 | 625 | 1.500 | 1.500 | 1.500 |

From a comparison between the catalyst without the second element (comparative catalyst A) and the catalyst of the present invention (B), it is evident that the system with two elements is more active operating at lower temperatures, with a higher selectivity value to $C_{25}^+$ (28.55 wt %), with decisively better hourly weight productivities to hydrocarbons with more than two carbon atoms (Prod. $C_2^+$) and yields to products containing carbon (Cobalt-Time-Yield=CoTY). More specifically, the CoTY is a useful parameter for comparing the catalysts with a different content of cobalt as it normalizes the yield to products containing carbon (hydrocarbons and $CO_2$) in relation to the moles of Co available.

CoTY=moles conv. CO/moles Co tot/h

The activities of the catalysts of the present invention (B and C) are almost the same even if an increase in the content of Sc causes an increase in the selectivity to hydrocarbons higher than $C_5$ as can be seen in Table 2. In example C, the lower selectivity to heavy $C_{25}^+$ hydrocarbons is influenced by the higher volumetric flow-rate of the reagent gas (GHSV=625).

On comparing the comparative catalyst E with the catalyst of the present invention D, having an intermediate content of Sc between B and C, it can be observed how with the same GHSV, catalyst D (2) gives higher values of CoTY, although operating at lower temperatures (210° C.), and selectivity to heavy hydrocarbons ($C_{25}^+$).

A comparison between catalyst D and comparative catalyst E also shows how higher temperatures cause the formation of lighter products. In fact, with the same CoTY, the lower temperature at which catalyst D(1) operates, allows lower $C_1$–$C_4$ selectivities and favours the selectivity to both $C_{25}^+$ and $C_5^+$.

EXAMPLE 6

Catalyst F

The silica used in example 1 is dry impregnated with a nitric solution of $Co(NO_3)_2.6H_2O$ in such quantities as to obtain a percentage of Co equal to 7.5% by weight referring to the total.

The silica thus impregnated is dried at 120° C. for 16 hours and calcined at 400° C. in air for 4 hours, then treated in a stream of hydrogen at a space velocity (GHSEI) of 1000 $h^{-1}$, in a tubular reactor at 400° C. for 16 hours. The sample thus reduced is passivated in a mixture (1%)$O_2$/(99%)$N_2$ with a GHSV at 1000 $h^{-1}$ for 2 hours at room temperature.

A $10^{-3}$ solution in acetone of $Sc(No_3)_2$ is added to this precursor, in such a volume as to obtain a final weight percentage of Scandium equal to 0.5%.

The suspension thus obtained is left under stirring for two hours and then dried under vacuum at 40° C. The sample is calcined at 300° C. for 4 hours in air, reduced at 400° C. in $H_2$ for 16 hours with a GHSV of 1000 $h^{-1}$ at room temperature and then passivated in (1%)$O^2$/ (99%)$N_2$ with a GHSV of 1000 $h^{-1}$ for 2 hours at room temperature.

The catalyst thus prepared (Co=7.5%, Sc=0.5) is tested for the Fischer-Tropsch reaction according to the above procedure. The results are shown in table 3, which indicates by comparison, the data obtained for the catalyst (catalyst G) described in example 18 of WO 93/05000 having the same composition (Co=7.5%; Sc=0.5%).

TABLE 3

| | Cat. F | Comp. Cat. G |
|---|---|---|
| Temperature (° C.) | 240 | 240 |
| Conversion CO (%) | 80.11 | 68 |
| Production $C_2^+$ (g/Kg/h) | 266.1 | 153 |
| Co-T-Y | 12.64 | — |
| Selectivity $C_2^+$ (w/w %) | 88.45 | 60 |
| Selectivity $CH_4$ (C %) | 11.55 | 35 |
| Selectivity $C_1$–$C_4$ (w/w %) | 18.52 | — |
| Selectivity $C_{10}$–$C_{24}$ (w/w %) | 49.52 | — |
| Selectivity $C_{25}^+$ (w/w %) | 23.33 | — |
| Selectivity $C_5^+$ (w/w %) | 81.48 | — |
| Selectivity $CO_2$ (w/w %) | 0.66 | 5 |
| GHSV | 1.000 | 1.000 |

The data of table 3 show how the two catalysts, one of the present invention and the other of the prior art, give completely different performances even though they have the same composition (7.5% of Co and 0.5% of Sc for both).

In fact, catalyst F of the present invention gives, with respect to the catalyst of the prior art, considerably higher conversions of CO and productivity to $C_2^+$, as well as much lower selectivity to methane.

What is claimed is:

1. A process for the preparation of a catalyst comprising an inert carrier selected from at least one oxide of at least one element selected from the group consisting of Si, Ti, Al, Zr, Zn, Mg, and Sn, in the form of elements or oxides, (cobalt, and X scandium in an amount less than the amount of cobalt, which comprises at least the following steps:

1) production of a first catalytic precursor (A) containing cobalt and at least part of the inert carrier, by the deposition of cobalt on the inert carrier; subsequent calcination, reduction and passivation of the inert carrier containing cobalt;

2) production of the final catalyst by the deposition of scandium on the catalytic precursor (A); subsequent calcination, reduction and passivation of the inert carrier containing cobalt and scandium.

2. The process according to claim 1, wherein the inert carrier is silica.

3. The process according to claim 1, wherein the catalyst has a content of cobalt of from 1 to 50% by weight and a content of scandium of from 0.05 to 5% by weight.

4. The process according to claim 3, wherein the cobalt is contained in a quantity of from 5 to 35% and the scandium in a quantity of from 0.1 to 3% by weight.

5. The process according to claim 1, wherein in step (1) the calcination is carried out at a temperature of from 350° C. to 450° C., whereas in step (2) the calcination is carried out at a temperature of from 250° C. to 350° C.

6. The catalyst which can be obtained according to claim 1.

7. A process for the synthesis of essentially linear and saturated hydrocarbons starting from synthesis gas comprising CO and $H_2$, which comprises reacting the synthesis gas with a catalyst prepared according to claim 1, at a pressure of from 0.1 to 15 MPa, the temperature being from 150° C. to 350° C., at an hourly volumetric velocity of from 100 to 20000 volumes of synthesis gas per volume of catalyst per hour, the molar ratio $H_2/CO$ in the synthesis gas being from 1:2 to 5:1.

8. The process according to claim 7, wherein the pressure is from 1 to 10 MPa, the temperature from 170° C. to 300° C., the hourly volumetric velocity from 400 to 5000 volumes of synthesis gas per volume of catalyst per hour, the ratio $H_2/CO$ in the synthesis gas is from about 1.2:1 to about 2.5:1.

9. The catalyst which can be obtained according to claim 2.

10. The catalyst which can be obtained according to claim 3.

11. The catalyst which can be obtained according to claim 4.

12. The catalyst which can be obtained according to claim 5.

13. A process for the synthesis of essentially linear and saturated hydrocarbons starting from synthesis gas comprising CO and $H_2$, which comprises reacting the synthesis gas with a catalyst prepared according to claim 2, at a pressure of from 0.1 to 15 MPa, the temperature being from 150° C. to 350° C., at an hourly volumetric velocity of from 100 to 20000 volumes of synthesis gas per volume of catalyst per hour, the molar ratio $H_2/CO$ in the synthesis gas being from 1:2 to 5:1.

14. A process for the synthesis of essentially linear and saturated hydrocarbons starting from synthesis gas comprising CO and $H_2$, which comprises reacting the synthesis gas with a catalyst prepared according to claim 3, at a pressure of from 0.1 to 15 MPa, the temperature being from 150° C. to 350° C., at an hourly volumetric velocity of from 100 to 20000 volumes of synthesis gas per volume of catalyst per hour, the molar ratio $H_2/CO$ in the synthesis gas being from 1:2 to 5:1.

15. A process for the synthesis of essentially linear and saturated hydrocarbons starting from synthesis gas comprising CO and $H_2$, which comprises reacting the synthesis gas with a catalyst prepared according to claim 4, at a pressure of from 0.1 to 15 MPa, the temperature being from 150° C. to 350° C., at an hourly volumetric velocity of from 100 to 20000 volumes of synthesis gas per volume of catalyst per hour, the molar ratio $H_2/CO$ in the synthesis gas being from 1:2 to 5:1.

16. A process for the synthesis of essentially linear and saturated hydrocarbons starting from synthesis gas comprising CO and $H_2$, which comprises reacting the synthesis gas with a catalyst prepared according to claim 5, at a pressure of from 0.1 to 15 MPa, the temperature being from 150° C. to 350° C., at an hourly volumetric velocity of from 100 to 20000 volumes of synthesis gas per volume of catalyst per hour, the molar ratio $H_2/CO$ in the synthesis gas being from 1:2 to 5:1.

* * * * *